(12) United States Patent
Ratcliffe et al.

(10) Patent No.: US 6,509,169 B2
(45) Date of Patent: Jan. 21, 2003

(54) DETECTION OF *HELICOBACTER PYLORI*

(75) Inventors: Norman M. Ratcliffe, Bristol (GB);
Clive Teare, Pucklechurch (GB);
Christopher Dunn, Dursley (GB);
David C. Cowell, Wooton-under-Edge (GB); Caroline Penault, Bristol (GB);
Paul Chambers, Ipswich (GB); Murdo M. Black, Ipswich (GB)

(73) Assignee: University of West England, Bristol, Bristol (GB)

( * ) Notice: Subject to any disclaimer, the term of this patent is extended or adjusted under 35 U.S.C. 154(b) by 0 days.

(21) Appl. No.: 09/903,902

(22) Filed: Jul. 12, 2001

(65) Prior Publication Data

US 2002/0090667 A1 Jul. 11, 2002

Related U.S. Application Data

(60) Provisional application No. 60/225,055, filed on Aug. 14, 2000.

(51) Int. Cl.$^7$ ............... C12Q 1/04; C12M 1/34

(52) U.S. Cl. .......... 435/34; 435/287.1; 435/287.5; 422/83

(58) Field of Search ............... 435/34, 287.1, 435/287.5; 422/83

(56) References Cited

U.S. PATENT DOCUMENTS

| | | | | |
|---|---|---|---|---|
| 3,852,036 | A | 12/1974 | Burroughs et al. | 422/84 |
| 4,093,945 | A | 6/1978 | Collier et al. | 180/272 |
| 4,947,861 | A | 8/1990 | Hamilton | 600/532 |
| 5,057,436 | A | 10/1991 | Ball | 436/113 |
| 5,364,797 | A | 11/1994 | Olson et al. | 436/501 |
| 5,719,052 | A | 2/1998 | Ito et al. | 435/287.1 |
| 6,067,989 | A * | 5/2000 | Katzman | 422/84 |
| 2002/0090667 | A1 * | 7/2002 | Ratcliffe | 435/34 |

FOREIGN PATENT DOCUMENTS

| | | |
|---|---|---|
| DE | 29902593 U1 | 8/1999 |
| EP | 0206133 A1 | 12/1986 |
| EP | 0302304 A2 | 2/1989 |
| EP | 0411793 A2 | 2/1991 |
| EP | 0679721 A1 | 11/1995 |
| GB | 2169608 A | 7/1986 |
| GB | 2234515 A | 2/1991 |
| JP | 59-123977 | 1/1986 |
| JP | H8-145991 | 6/1996 |
| WO | 85/00888 | 2/1985 |
| WO | 91/07659 | 5/1991 |
| WO | 91/19192 | 12/1991 |
| WO | 97/30351 | 8/1997 |

OTHER PUBLICATIONS

Bercik et al., Am. J. Gastroenterol., vol. 95, *The effect of ammonia on omeprazole–induced reduction of gastric acidity in subjects with Helicobacter pylori infection*, pp. 947–955, 2000.

D'Elios et al., Int. J. Immunopath. & Pharmacol., vol. 13, *Usefulness of 13C–urea breath test in the diagnosis of gastric Helicobacter pylori infection*, pp. 27–30, 2000.

(List continued on next page.)

*Primary Examiner*—Louise N. Leary
(74) *Attorney, Agent, or Firm*—Thompson Coburn LLP

(57) ABSTRACT

A method for detecting *Helicobacter pylori* in a subject's gastroenteral tract involves measuring a change in resistance of an electronic or electrochemical sensor, notably a polypyrrole film, on exposure to gas from the subject's lungs and/or stomach. Depending on the magnitude of the change (if any) a positive or negative result is indicated visually by electronics means. Two sensors are used, one of which receives a sample of gas which has passed through an amonia-absorbing means to provide a corrected baseline value for the ammonia. The invention also provides apparatus suitable for carrying out the method.

13 Claims, 5 Drawing Sheets

OTHER PUBLICATIONS

Fitzgerald et al., Irish Journal of Medical Science, vol. 292, *Studies on the physiological chemistry and clinical significance of urease and urea with special reference to the stomach*, pp. 97–159, 1950.

Gustafsson et al., Synthetic Metals, vol. 31, *The interaction between ammonia and poly(pyrrole)*, pp. 163–179, 1989.

Heading, Gut, vol. 25, *Antacids and duodenal ulcer*, p. 1195–1198, 1984.

Hu et al., Infection and Immunity, vol. 58, *Purification and N–terminal analysis of urease from helicobacter pylori*, pp. 992–998, 1990.

Ito et al., Lancet, vol. 346, *Hyperammonaemia and helicobacter pylori*, pp. 124–125, 1995.

Krumbiegel et al., Scand. J. Gastroentrol., vol. 35, *Diagnosis of helicobacter pylori infection in children: Is the $^{15}N$ urine test more reliable than the $^{13}C$ breath test*, pp. 353–358, 2000.

Ratcliffe, Analytica Chimica Acta, vol. 239, *Poypyrrole--based sensor for hydrazine and ammonia*, pp. 257–262, 1990.

Ratcliffe, Synthetic Metals, vol. 38, *The simple preparation of a conducting and transparent polypyrrole film*, pp. 87–92, 1990.

Teitz, Fundamentals of Clinical Chemistry, *Gastric, pancreatic and intestinal function*, Baltimore, WB Saunders Company, pp. 1063–1099, 1976.

Vaira et al., Lancet, vol. 354, *Diagnosis of helicobacter pylori infection with a new non–invasive antigen–based assay*, pp. 30–33, 1999.

Von Korff, et al., Am. J. Physiol, vol. 165, *Role of urease in the gastric mucosa, III Plasma urea as source of ammonia ion in gastric juice of histamine–stimulated dog*, pp. 695–700, 1951.

Washington, Chemist and Druggist, vol. 234, *The acid test*, pp. 1026 and 1028, 1990.

\* cited by examiner

DETECTION OF *HELICOBACTER PYLORI*

This application claims the benefit of U.S. Provisional application Serial No. 60/225,055, filed Aug. 14, 2000.

FIELD OF THE INVENTION

The present invention relates to a device and method for detecting *Helicobacter Pylori* in human subjects.

BACKGROUND OF THE INVENTION

It has been known for some time that infection by *Helicobacter pylori* (*H pylori*) may increase the risk of a subject suffering from illnesses such as gastritis and duodenitis, and from peptic and duodenal ulcers. Detection of *H pylori* is therefore desirable to determine whether patients have, or have increased risk of having, such illnesses, and to enable appropriate treatment to be given.

*H pylori* produces ammonia and carbon dioxide by the action of a urease on urea in bodily fluids, and various tests have been proposed to detect *H pylori* by detecting the products of this reaction.

A test which is currently in use involves administering $^{13}C$-labelled urea to the subject and subsequently testing carbon dioxide in the subject's breath for the presence of $^{13}C$. However, testing for $^{13}C$ requires a sample to be sent away for laboratory testing, which is slow and relatively expensive.

Various methods are known for diagnosing the presence of *H pylori* in human subjects. In U.S. Pat. No. 4,947,861 it was proposed to detect the presence of ammonia in a subject's breath following oral administration of urea. The method comprises collecting a sample of alveolar air at least ten minutes after administration of the urea, passing the air over an alkaline hygroscopic material to remove water vapour, and passing the dried alveolar air to a sensor which indicates the presence of ammonia. The sensor described is a glass tube filled with a granular material that changes colour as ammonia is passed through it. DE 299 02 593 U1 describes the use of an electronic "nose" for detecting infection by *H pylori*, and other conditions such as lactose intolerance, enzyme shortages, bacterial or viral infections. The electronic nose produces a fingerprint which is compared with a stored databank to produce a diagnosis. U.S. Pat. No. 5,719,052 describes a method and apparatus for collecting gas from a subject's stomach by stimulating the subject's vomiting reflex.

International Patent Application WO 97/3035 describes various chemical indicators which change colour in the presence of ammonia to provide a visible indicator of ammonia in a subject's breath.

It is desirable to have a detection device and method for detecting *H pylori* which is non-invasive, speedy, and which can be used by a patient or other person without medical supervision.

SUMMARY OF THE INVENTION

According to a first aspect of the present invention there is provided a method for detecting the presence of *Helicobacter pylori* in the gastroenteral tract of a subject, the method comprising the steps of:

a) obtaining a volume of gas from the lungs and/or stomach of the subject;

b) dividing the said volume of gas into first and second substantially equal portions;

c) causing or permitting the first said portion of gas to come into intimate contact with a first electronic or electrochemical ammonia sensor connected to means for measuring the electrical resistance of the said first sensor;

d) causing or permitting the second said portion of gas to come into intimate contact with ammonia absorbing means and then into intimate contact with a second electronic or electrochemical ammonia sensor connected to means for measuring the electrical resistance of the said second sensor;

e) measuring the resistance of the first and second sensors when in contact with the said portions of gas;

f) comparing the said resistances of the sensors to produce a compared value; and g) producing a visible output signal to indicate a positive or negative diagnosis of *Helicobacter pylori* infection according to whether or not the compared value exceeds a predetermined threshold value.

The method is non-invasive, and it can be speedy and easy for a patient or other subject to self-administer. It is not necessary to administer urea to the subject prior to carrying out the method.

An antacid (for example magnesium hydroxide) may be administered orally prior to testing. This will promote conversion of ammonium ions in the stomach to gaseous ammonia If the antacid is a carbonate or bicarbonate (for example sodium bicarbonate), it will also produce carbon dioxide to facilitate eructation.

A pair of similar sensors are provided, each in its own chamber. The gas is distributed substantially equally between the two chambers, but one chamber has an ammonia-absorbing barrier through which gas passes before coming into contact with the sensor. Electronics means compare the difference between or ratio of resistances of the two sensors and express the result as a visible output. The output could be numeric, but is preferably in the form of a signal corresponding to either a positive or a negative diagnosis. For example, a green light or a red light could be illuminated.

To further increase the sensitivity of the device, the gas could be passed through an alkaline desiccant (for example solid sodium hydroxide) in known manner, to remove water vapour (and some carbon dioxide) before the gas enters the chambers.

A preferred sensor comprises a film of polypyrrole, which is connected by electrodes to a suitable meter. Methods of making polypyrrole films suitable for use in the invention are described in GB 2 234 515 and EP 0 206 133. The film preferably has a thickness in the range 50 to 250 $\mu$m.

According to another aspect of the present invention there is provided a detection device for measuring ammonia content in gas from a subject's lungs and/or stomach, the device comprising:

a) a first chamber and a second chamber, each of which has an entrance opening for receiving the said gas, and each of which houses an electronic or electrochemical ammonia sensor connected to means for measuring the electrical resistance of the sensor;

b) the entrance openings of the chambers being connected to an inlet, the arrangement being such that incoming gas from the inlet will be divided into two substantially equal portions, each of which will pass through a corresponding entrance opening;

c) means for comparing the resistance of both sensors to produce a compared value;

d) means for producing a visible output signal according to whether the compared value exceeds a predetermined threshold value; and e) wherein the second chamber is provided with means for absorbing ammonia, located between the entrance opening thereto and the sensor therein whereby at least some gas which enters the second chamber through the entrance opening will pass through the ammonia-absorbing means.

Although the term "ammonia-absorbing means" is used herein for convenience, it will be understood that this term includes any means which remove ammonia from the gas. Thus, the term includes amonia adsorbents and materials which chemically combine with ammonia.

A preferred ammonia sensor comprises a film of polypyrrole, connected by electrodes to a suitable meter.

In a preferred embodiment, each chamber is provided with an exit vent to facilitate the passage of gas therethrough.

To reduce the volume of "dead space" in the chambers, they may optionally be constructed to be expandable, for example by having elastic walls, by being of telescopic construction, or by having a movable plunger, like a syringe. By reducing dead space, and therefore dilution of the gas portions, the sensitivity of the method can be increased.

BRIEF DESCRIPTION OF THE DRAWINGS

The invention will now be further described, by way of example, with reference to the following drawings in which.

DETAILED DESCRIPTION

Figure 1:
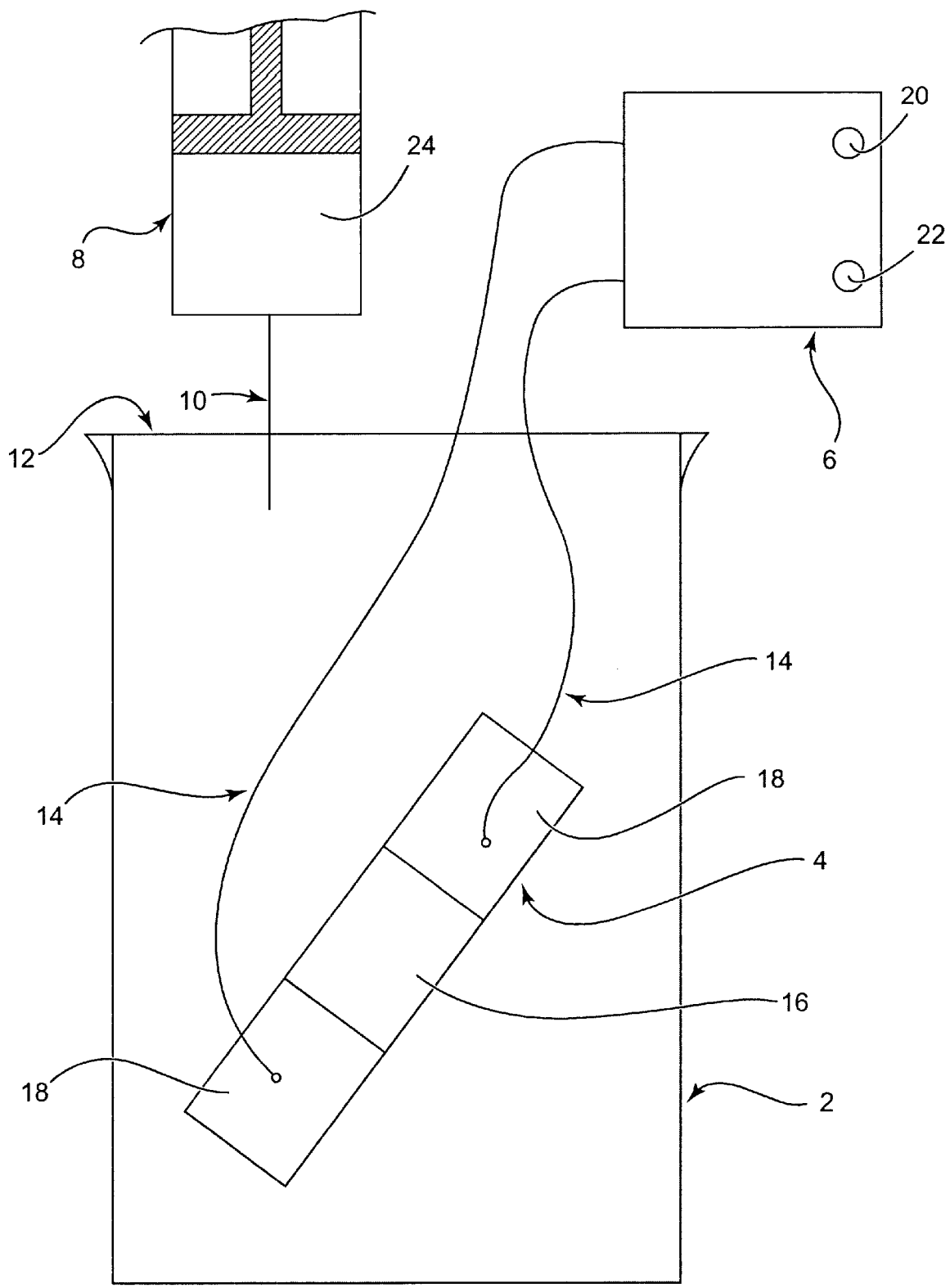
FIG. 1 is a schematic representation of one chamber of an ammonia detection device in accordance with an aspect of the present invention.

The experimental device for detecting gaseous ammonia shown in FIG. 1 comprises a chamber 2 in which is housed an ammonia sensor 4. The sensor 4 comprises a polypyrrole film 16, about 50 $\mu$m thick, which changes its electrical resistance in the presence of ammonia The film 16 is carried on a pcb-type conductive board, for example Veroboard™, which has been etched to remove conductive material completely across the middle of the sensor 4, so that the two ends 18 of the board are not in electrical contact with each other. An insulating film of PEEK is disposed between the film 16 and the conductive board. The film 16 is in electrical contact at opposed edges with each conductive end portion 18. The end portions 18 are each connected by wires 14 to a meter 6 which measures electrical resistance across the film 16. In practice, a corresponding chamber will be provided, illustrated in FIG. 4, which is of similar construction but which includes an ammonia-absorbing material. This provides a corrected baseline value.

The inside of the chamber 2 is maintained at 100% humidity and sealed by clingfilm, in this example Nesco-film™. When the device is used in the method of the invention, a sample of gas 24 from a subject's lungs and/or stomach is collected in a syringe 8 and introduced into the chamber 2 via a needle 10. The meter 6 records the electrical resistance of the polypyrrole film 16 before the gas 24 is introduced into the chamber 2, and again after the gas has been introduced. The meter 6 then compares the resistances to produce a compared value and lights up an LED 20 or 22 according to whether the compared value is above or below a predetermined threshold. The meter 6 may measure the difference in resistance, or a ratio of resistances. The threshold value is calibrated to be just below the value produced by samples from test subjects known to be infected with *H pylori*. If the LED 22 lights up, showing a value which corresponds to infection, the subject knows to seek appropriate treatment or confirmatory alternative testing.

Figure 2:
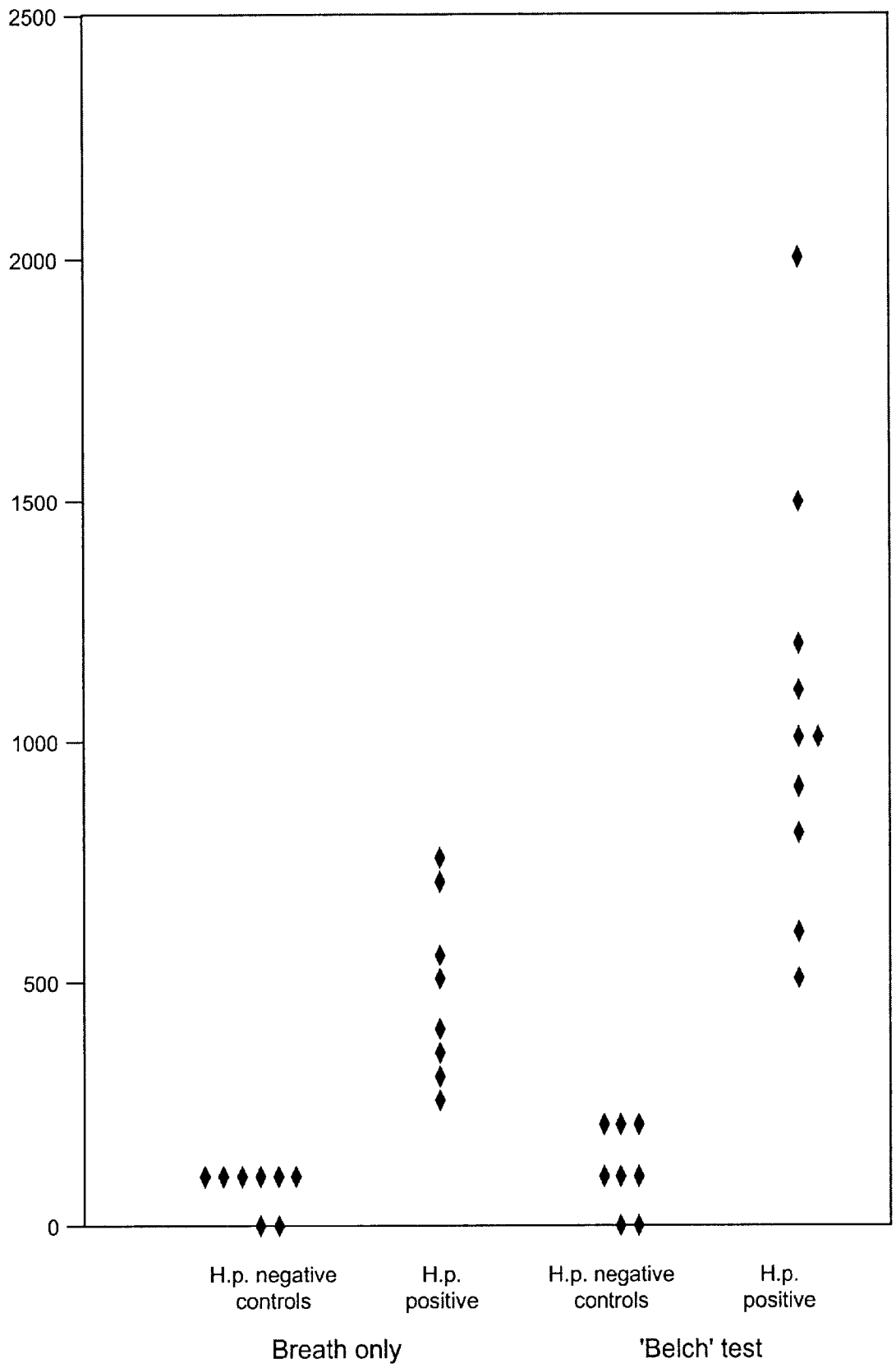
FIG. 2 is a graph showing change in resistance of the device of FIG. 1, for different subjects.

FIG. 2 shows test results for two groups of control subjects, one group known to be *H pylori* negative and the other *H pylori* positive. In each case, a 10 ml sample of gas 24 was collected and introduced into a chamber of about 10 to 15 ml volume. The film 16 was 10 mm square. The two sets of results on the left are for a breath test only, and the two sets of results on the right (the 'belch test') are for gas collected from subjects' stomachs, following ingestion of sodium bicarbonate in water. In each case, there is a clear threshold between the measured resistance for the negative and positive groups.

Figure 3:
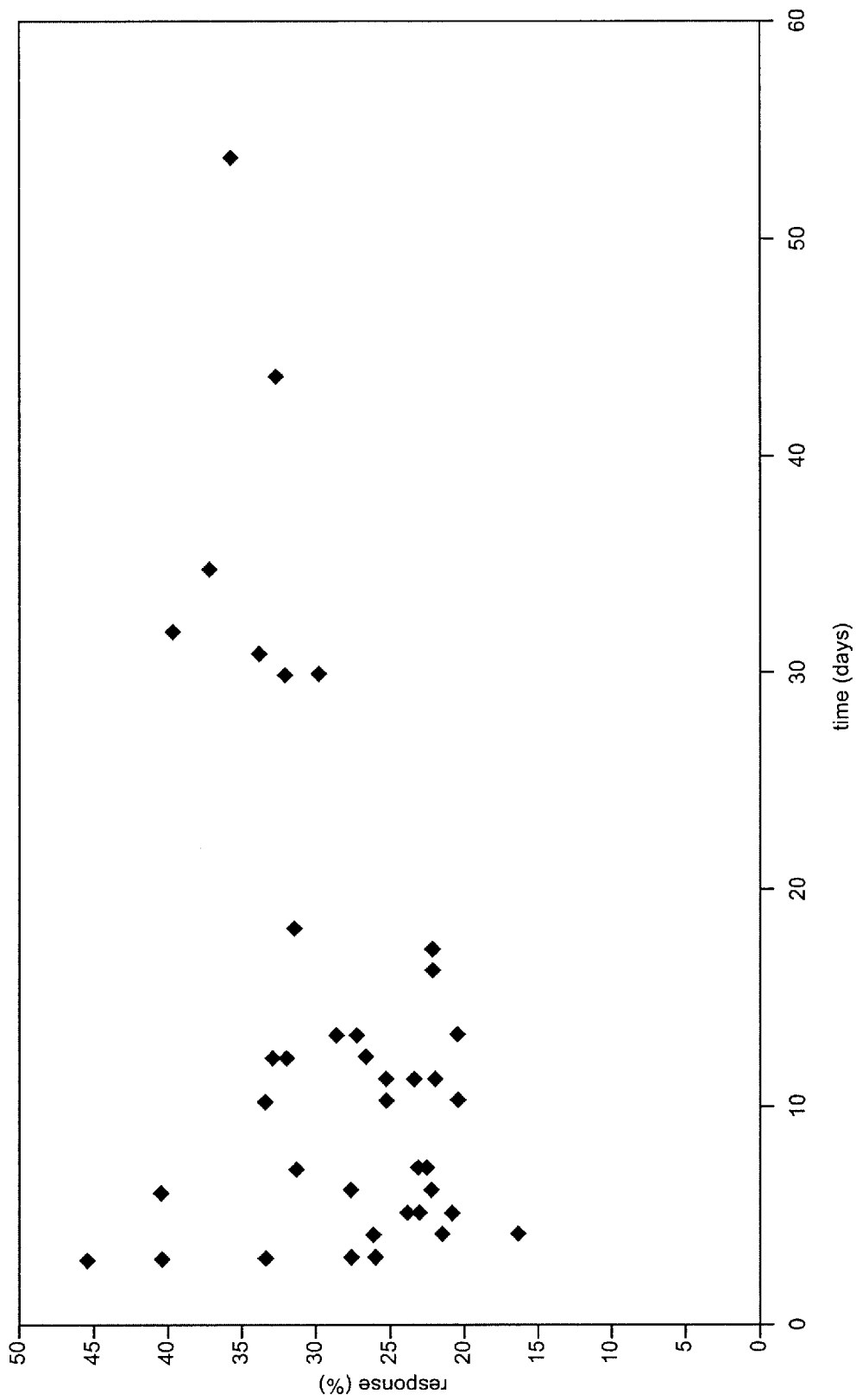
FIG. 3 is a graph of response against time for the device of FIG. 1.

The same test conditions were used to check the response of sensors over time, but using a known concentration (100 ppm)of ammonia in air. The sensors were maintained at 100% humidity. The results are shown in FIG. 3, with percentage change in resistance being plotted against the time (days) in which the sensor 4 was maintained in the chamber 2 prior to the measurement being taken. For all times up to 60 days, the percentage change was at least 15%.

Figure 4:
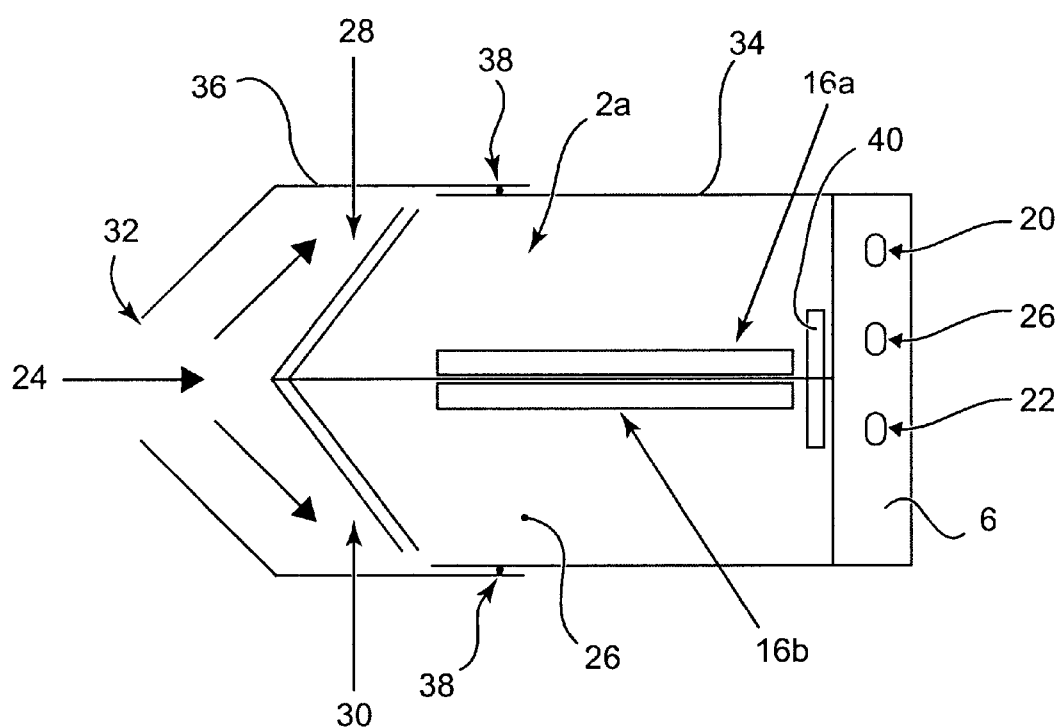
FIG. 4 is a schematic representation of an ammonia detection device in accordance with the present invention.

The device shown in FIG. 4 comprises a first chamber 2a housing a first sensor 16a, and a second chamber 2b housing a second sensor 16b. The chambers 2a and 2b are formed from an inner tubular member 34 and an outer tubular member 36 with a gas-tight seal 38 therebetween. Because the tubular members 34, 36 are telescopically nested together, the chambers 2 can expand as gas is introduced into them, thereby reducing dead space. The chambers 2 and sensors 16 are of identical shape and construction. The first chamber has an entrance opening which is substantially occupied by a first porous frit 28, and the second chamber has an entrance opening which is substantially occupied by a second porous frit 30. The frits 28, 30 are arranged and composed such that each provides substantially the same resistance to the passage of gas 24 which is provided through a common entrance opening 32,for example by a subject breathing through that entrance. Each chamber may optionally be provided with a vent opening (40) to facilitate the flow of gas through the chambers. The second frit 30 is provided with means for absorbing ammonia, for example sodium dihydrogen phosphate or copper sulphate crystals, so that at least some of the ammonia (and preferably substantially all of the ammonia) which may be present in gas 24 blown into the second chamber 2b is absorbed in the second frit 30 and does not reach the second sensor 16b. The first frit 28 does not significantly absorb ammonia, so that ammonia which is present in gas 24 blown into the first chamber 2a reaches the first sensor 2a.

Both sensors 16 are connected by wires (not shown) to an integral meter 6. The meter 6 is optionally provided with means (not shown) for detecting gas f low in the chambers 2 . A first LED 26 on the meter 6 lights up when it detects the passage of gas 24. The meter 6 measures the resistance of both sensors and produces a compared value which is the ratio of the resistances. The meter 6 displays a visible output accordingly, by illuminating (green) LED 20 corresponding to a negative test for H pylori, or (red) LED 22 corresponding to a positive test.

Based on data from in vitzo studies, five healthy H. pylori-negative volunteers (determined by the $^{13}$C breath test) were studied. In this work, the polypyrrole film was fabricated by dip coating a colloidal suspension of poly (pyrrole), after chemical oxidation of the pyrrole monomer, on an acrylic sheet using known methods (Ratcliffe NR. Poly(pyrrole)-based sensor for hydrazine and ammonia. *Analytica Chimica Acta* 1990; 239: 257–262; Ratcliffe NR. The simple preparation of a conducting and transparent poly(pyrrole) film. *Synthetic Metals* 1990; 38: 87–92).

The resultant film, approximately 50 nm thick, has a surface topography (revealed by transmission electron and atomic force microscopy) composed of spheres in intimate contact with each other. The volunteers were studied twice in random order on two separate days after an overnight fast; once after ingestion of an empty gelatin capsule and once after ingestion of a capsule containing 10 mg of $NH_4Cl$. Three additional volunteers were studied only after ingestion of $NH_4Cl$. Ten minutes after the capsule (a time sufficient for capsule degradation according to pharmacopoeia standards and our own in vitro observations), each subject swallowed a mixture of 15 ml of Milk of Magnesia® (BCM Ltd, Nottingham: containing 415 mg of $Mg(OH)_2$ per 5 ml) and 50 ml of water and, a further ten minutes later, drank 100 ml of sparkling water to 'drive off' any $NH_3$. Mouth air samples (10 ml) were collected into a syringe at baseline (before the capsule); immediately prior to the Milk of Magnesia®/water mixture; and, finally, ten minutes after the 100 ml of sparkling water. These samples were individually expelled into a vial containing the $NH_3$ sensor linked to a multimeter (measuring resistance) as described above. Pilot studies suggested, in contrast to in vitro data, that cold (4° C.) sparkling water was superior to still water, so the former was used in all in vivo studies.

Five patients (three males and two females) who tested positive for *H. pylori* with at least one clinically-validated test (e,g., $^{13}$C breath test, serology) underwent the same procedure but without taking $NH_4Cl$.

Figure 5:
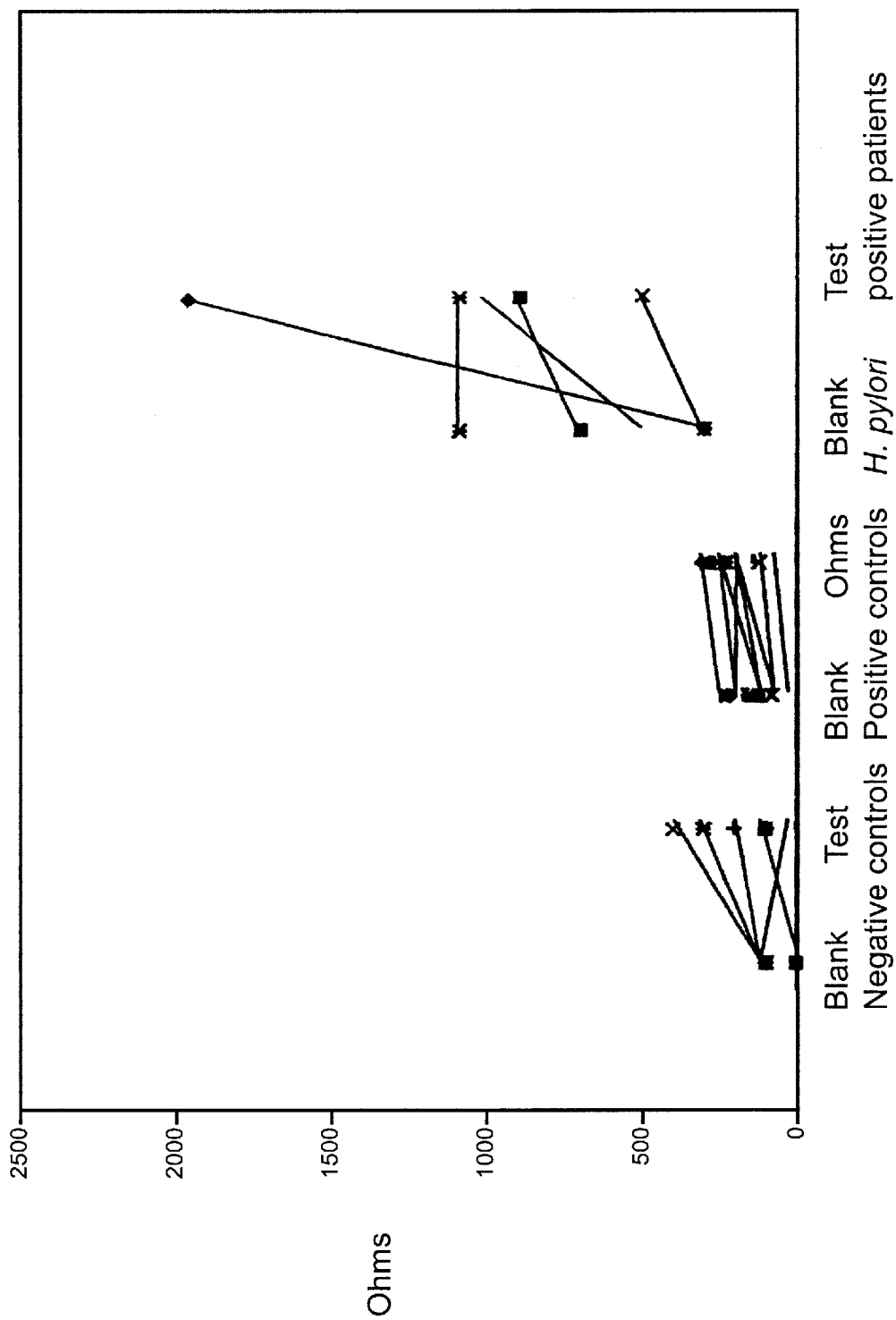
FIG. 5 shows changes in electrical resistance measurement results for subjects under a defined test protocol.

In vivo studies: *H. pylori*-negative subjects FIG. 5 summarises the changes in sensor chemoresistivity of mouth air in *H. pylori*-negative subjects who had ingested 10 mg $NH_4Cl$ or an empty gelatin capsule. FIG. 5 shows changes in electrical resistance for subjects exposed to mouth air from *H pylori*-negative subjects ("negative" controls), *H pylori*-negative subjects after ingestion of 10 mg ammonia chloride ("positive controls") and *H pylori*-positive patients. On average, $NH_3$ levels detected in mouth air after ingestion of the $NH_4Cl$-containing capsule, but prior to administration of the Milk of Magnesia/water mixture, were almost twice those seen after ingestion of the placebo. Furthermore, these data were obtained Without the subjects necessarily belching.

In vivo studies: *H. pylori*-positive patients Five *H. pylori*-positive patients underwent the test protocol without taking the $NH_4Cl$-containing capsule. The results are also shown in FIG. 5. Pre-protocol $NH_3$ levels in the patients' mouths were higher than the baseline levels measured in the *H. pylori*-negative subjects who ingested $NH_4Cl$ ("positive controls"). Furthermore, even higher levels were recorded in the four patients in whom the test protocol produced a belch. None of the healthy volunteers or the *H. pylori*-positive patients experienced any adverse effects from the study.

The device and method of the present invention can detect sub-ppm concentrations of $NH_3$ in 'endogenous' mouth air, and can provide a point-of-care diagnostic test for *Helicobacter pylori* without the need for patients to ingest urea, and with the results being immediately available to the attending physician. Furthermore, the conditions necessary for the bacteria-associated $NH_4^+$to be converted to $NH_3$ and liberated through the oral cavity can be achieved through the use of an established antacid and cold, sparkling water with no adverse reactions amongst the small number of healthy subjects and *H. pylori*-positive patients so far tested.

Studies in the healthy volunteers clearly showed that $NH_3$ levels in mouth air after ingestion of 10 mg $NH_4Cl$ were generally higher than in the same subjects tested without ingestion of $NH_4Cl$ (FIG. 5). This difference was evident irrespective of whether or not the subjects belched. Removing the requirement to belch is seen as a significant advantage for a diagnostic test as, in a study with a larger number of normal subjects, only a proportion were induced to belch reliably under our current protocol.

Given the small number of subjects tested, there is some overlap in the data between those who ingested $NH_4CL$ and those given the placebo. However, the data in FIG. 5 show markedly higher levels of mouth $NH_3$ in the overnight fasted *H. pylori*-positive patients than in either group of controls. Thus, the patients had higher baseline (without the need to belch) $NH_3$ levels than the healthy subjects even after the latter had ingested 10 mg $NH_4Cl$. Furthermore, four of the five patients did belch and, in each case, this was associated with even higher mouth $NH_3$ levels. All these in vivo data were acquired without any subject or patient being required to ingest urea. The data also suggest that intra-gastric levels of $NH_3$ in patients with *H. pylori* infection are considerably higher than those attained by the ingestion of 10 mg of $NH_4Cl$.

The invention provides a rapid, point-of-care diagnostic test for *H. pylori* based on the chemiresistive detection of $NH_3$ in mouth air. The proposed test does not require patients to ingest urea, and appears to be possible on 'endogenous' mouth air without the need for the patient to belch or even to ingest the antacid/water mixture. Additionally, the test method uses neither stable nor radioactive isotopes thus obviating the need to send samples to a central laboratory for analysis, and overcoming difficulties associated with radioisotopes.

While the invention has been described with reference to specific embodiments thereof, it is to be understood that the invention is not limited to the described embodiments. Many variants may be made within the spirit and scope of the invention.

We claim:

1. A method for detecting the presence of *Helicobacter pylori* in the gastroenteral tract of a subject, the method comprising the steps of:
    a) obtaining a volume of gas from the lungs and/or stomach of the subject;
    b) dividing the said volume of gas into first and second substantially equal portions;
    c) causing or permitting the first said portion of gas to come into intimate contact with a first electronic or electrochemical ammonia sensor connected to means for measuring the electrical resistance of the said first sensor;
    d) causing or permitting the second said portion of gas to come into intimate contact with ammonia absorbing means and then into intimate contact with a second electronic or electrochemical ammonia sensor connected to means for measuring the electrical resistance of the said second sensor;

e) measuring the resistance of the first and second sensors when in contact with the said portions of gas;

f) comparing the said resistances of the sensors to produce a compared value; and g) producing a visible output signal to indicate a positive or negative diagnosis of *Helicobacter pylori* infection according to whether or not the compared value exceeds a predetermined threshold value.

2. A method as claimed in claim 1, wherein substantially all of the said second portion of gas passes through the said ammonia absorbing means before coming into contact with the said second ammonia sensor so that substantially all of the ammonia which may be present in the said second portion of gas is absorbed by the ammonia absorbing means.

3. A method as claimed in claim 1, wherein each of the said ammonia sensors is housed in a chamber and entrance of a portion of gas into the said chamber causes the chamber to expand.

4. A method as claimed in claim 1, wherein an antacid is administered orally to the subject prior to obtaining the gas from the subject's lungs and/or stomach.

5. A method as claimed claim 1, wherein sparkling water is administered orally to the subject prior to obtaining the gas from the subject's lungs and/or stomach.

6. A detection device for measuring ammonia content in gas from a subject's lungs and/or stomach, the device comprising:

a) a first chamber and a second chamber, each of which has an entrance opening for receiving the said gas, and each of which houses an electronic or electrochemical ammonia sensor connected to means for measuring the electrical resistance of the sensor;

b) the entrance openings of the chambers being connected to an inlet, the arrangement being such that incoming gas from the inlet will be divided into two substantially equal portions, each of which will pass through a corresponding entrance opening;

c) means for comparing the resistance of both sensors to produce a compared value;

d) means for producing a visible output signal according to whether the compared value exceeds a predetermined threshold value; and e) wherein the second chamber is provided with means for absorbing ammonia, located between the entrance opening thereto and the sensor therein whereby at least some gas which enters the second chamber through the entrance opening will pass through the ammonia-absorbing means.

7. A device as claimed in claim 6, wherein each chamber is provided with a frit or baffle, each of which provides a substantially equal resistance to the passage of gas.

8. A device as claimed in claim 7, wherein the said ammonia-absorbing means is provided on the frit or baffle associated with the second chamber.

9. A device as claimed in claim 6, wherein each chamber is provided with an exit vent to facilitate the passage of gas therethrough.

10. A device as claimed in claim 6, wherein the ammonia-absorbing means comprises sodium dihydrogen phosphate or copper sulphate.

11. A device as claimed in claim 6, further including detection means for detecting the passage of breath one or both chambers, and display means responsive to said detection means.

12. A device as claimed in claim 6, which is arranged and constructed so that substantially all of the gas which comes into contact with the second sensor via the entrance opening of the second chamber will pass through the ammonia-absorbing means.

13. A device as claimed in claim 6, wherein each chamber is expandable.

* * * * *

UNITED STATES PATENT AND TRADEMARK OFFICE
CERTIFICATE OF CORRECTION

PATENT NO. : 6,509,169 B2
DATED : January 21, 2003
INVENTOR(S) : Norman M. Ratcliffe et al.

It is certified that error appears in the above-identified patent and that said Letters Patent is hereby corrected as shown below:

Title page,
Item [73], Assignee, should read as follows:
-- Assignee(s):  Hypoguard Limited
                 Dock Lane
                 Melton
                 Woodbridge
                 Suffolk, IP12 1PE, United Kingdom --

Signed and Sealed this

Fourteenth Day of December, 2004

JON W. DUDAS
*Director of the United States Patent and Trademark Office*